United States Patent
Malvasio

(10) Patent No.: US 6,598,433 B1
(45) Date of Patent: Jul. 29, 2003

(54) ANTI-THEFT DEVICE FOR A DEVICE HAVING A FLEXIBLE TUBE MEMBER

(76) Inventor: Frank A. Malvasio, 559 Sawgrass Corporate Pkwy., Sunrise, FL (US) 33325

( * ) Notice: Subject to any disclaimer, the term of this patent is extended or adjusted under 35 U.S.C. 154(b) by 0 days.

(21) Appl. No.: 09/777,005

(22) Filed: Feb. 5, 2001

(51) Int. Cl.[7] .............................................. E05B 73/00
(52) U.S. Cl. ..................... 70/18; 70/19; 70/58; 70/59; 70/61
(58) Field of Search ................... 70/14, 18, 19, 70/54–56, 58, 59, 61, 62, 201–203, 416

(56) References Cited

U.S. PATENT DOCUMENTS

| | | | | |
|---|---|---|---|---|
| 530,456 A | * | 12/1894 | Raymond ........................ 70/18 |
| 924,824 A | * | 6/1909 | Peebler ........................... 70/18 |
| 1,793,432 A | * | 2/1931 | Sczepczenski ............. 70/18 X |
| 2,668,645 A | * | 2/1954 | Pease ......................... 70/18 X |
| 3,444,547 A | | 5/1969 | Surek ........................... 340/280 |
| 3,905,214 A | * | 9/1975 | Bell ................................. 70/58 |
| 4,057,986 A | | 11/1977 | Zolke et al. ................... 70/233 |
| 4,146,242 A | * | 3/1979 | Bose ........................... 70/58 X |
| 4,300,690 A | * | 11/1981 | Thomas ...................... 70/59 X |
| 4,472,952 A | | 9/1984 | Hollowell, Jr. ................. 70/61 |
| 4,608,965 A | | 9/1986 | Anspach, Jr. et al. ........... 128/4 |
| 4,640,420 A | * | 2/1987 | McKay ....................... 70/59 X |
| 4,881,386 A | * | 11/1989 | Glines ............................ 70/19 |
| 4,953,371 A | * | 9/1990 | Appelbaum ................. 70/53 X |
| 4,991,413 A | * | 2/1991 | Arnaldo ........................... 70/19 |
| 5,027,622 A | * | 7/1991 | Hatch et al. .................... 70/14 |
| 5,154,072 A | * | 10/1992 | Leyden ........................... 70/18 |
| 5,193,366 A | * | 3/1993 | Brinkman ....................... 70/18 |
| 5,259,220 A | * | 11/1993 | Fredrickson ................... 70/14 |
| 5,347,833 A | * | 9/1994 | Branscum ...................... 70/59 |
| 5,501,555 A | | 3/1996 | Muetschele et al. ........ 70/61 X |
| 5,529,235 A | | 6/1996 | Boiarski et al. ......... 227/175.1 |
| 5,676,000 A | * | 10/1997 | Chen ......................... 70/211 X |
| 5,701,769 A | | 12/1997 | Hall ............................... 70/19 |
| 5,775,747 A | * | 7/1998 | Navarsky .................. 70/211 X |
| 5,806,350 A | * | 9/1998 | Savinsky ........................ 70/18 |
| 5,829,800 A | | 11/1998 | Stoltz et al. ................. 292/316 |
| 5,836,002 A | | 11/1998 | Morstein et al. ............. 340/568 |
| 5,934,112 A | * | 8/1999 | Rice et al. ...................... 70/18 |
| 6,018,968 A | * | 2/2000 | Sides ............................. 70/14 |
| 6,053,016 A | * | 4/2000 | Young ....................... 70/58 X |
| 6,212,919 B1 | * | 4/2001 | Gerow ............................ 70/18 |

FOREIGN PATENT DOCUMENTS

FR 602103 * 3/1926 .................. 70/200

* cited by examiner

Primary Examiner—Suzanne Dino Barrett
(74) Attorney, Agent, or Firm—Malin, Haley & DiMaggio, P.A.

(57) ABSTRACT

An anti-theft device for an endoscope, boroscope or other device is disclosed. The anti-theft device in one embodiment comprises a top portion with a channel through it and a bottom portion hingeably attached to the top portion. A locking mechanism presses the flexible tube against a resting surface. The bottom portion comprises a flange that extends into the top portion when the device is closed. A locking lip turns upon activation of the locking mechanism and extends above the flange when the device is closed, and a cam within the bottom portion pushes a bolt attached to the pressing surface upon activation of the locking mechanism, thereby pressing the flexible tube against the resting surface.

17 Claims, 3 Drawing Sheets

ANTI-THEFT DEVICE FOR A DEVICE HAVING A FLEXIBLE TUBE MEMBER

BACKGROUND OF THE INVENTION

1. Field of the Invention

This invention relates generally to the field of anti-theft devices and particularly to a anti-theft device for endoscopes and boroscopes and other devices having flexible tube members.

2. Description of Related Art

The use of endoscopes for medical purposes is well known. Endoscopes are relatively expensive and typically cost about $20,000 each. In certain specialized applications the cost of the endoscope is even greater. The characteristics of endoscopes allow them to be both portable and highly valuable for resale. Thus, it comes as little surprise that the medical industry has been plagued with a continuously increasing number of endoscope thefts. Research indicates that this theft is of epidemic proportion in the health care industry in the United States and around the world. It has been reported that at one medical center, twelve (12) endoscopes worth over $300,000 were lost in a single theft. In addition to the significant financial loss, the theft of these devices also means that they are not available when they may be needed in an emergency. Thus, what is needed in the art is an anti-theft device for endoscopes, boroscopes and other devices having flexible tube members. It is therefore to this effective resolution that the present invention is directed.

BRIEF SUMMARY OF THE INVENTION

The present invention provides an anti-theft device which is attached to a flexible tube member, such as those found on endoscopes, boroscopes and other devices, and secures such device by placing a locking portion of the anti-theft device over the tube or flexible portion of the item to be secured. The tube is placed in a channel defined by the top portion of the anti-theft device, and the top portion is closed against the bottom portion. The tube is then pressed by a pressing surface against a resting surface. When the locking mechanism is activated, a locking lip on the top and a flange on the bottom overlap as the pressing surface presses. Thus, the endoscope cannot be removed from the anti-theft device, and the anti-theft device can be secured to the wall.

In one embodiment of the present invention, the anti-theft device includes a top portion, a bottom portion hingeably attached to the top portion, a channel extending through the top portion, and a locking mechanism on the top portion. A pressing surface and a resting surface are provided, preferably within the top portion. The pressing surface, upon activation of the locking mechanism, presses the tube portion of the device to be locked against the resting surface.

The bottom portion preferably includes a flange that extends into the top portion when the device is closed. A locking lip turns upon activation of the locking mechanism. Activation is preferably by key. The locking lip extends above the flange when the device is closed. To prevent movement of the tube within the channel, a cam disposed within the top portion pushes a bolt attached to the pressing surface, causing the pressing surface to force the tube tightly against the resting surface.

The anti-theft device can include a means for attaching the locking lip and the cam to the locking mechanism. The top portion preferably includes a plate that fits over the locking mechanism and is attached to the top portion. The plate can include a slit that fits the flange when the device is closed. An additional slit can be disposed adjacent to the flange for ease of manufacture.

The anti-theft device can further include a sensor which triggers an alarm if the anti-theft device attached to the tube portion is removed for its intended storage area. The anti-theft device can also include a means for securing preferably associated with the bottom portion of the anti-theft device.

Accordingly, it is an object of the present invention to provide an anti-theft device for endoscopes, boroscopes and other devices having flexible tube members.

It is another objection of the present invention to provide an anti-theft device that is relatively small but effective to deter theft and is suited for attachment to the tube portion of an endoscope, boroscope or other device.

It is still another object of the present invention to provide an anti-theft device that effectively locks an endoscope, boroscope or other device having a flexible tube portion, while also permitting an authorized person to relatively quickly access the endoscope and unlock the anti-theft device.

It is even still another objection of the present invention to provide an anti-theft device that is relatively easy to manufacture and use.

In accordance with these and other objects which will become apparent hereinafter, the instant invention will now be described with particular reference to the accompanying drawings.

Figure 1:
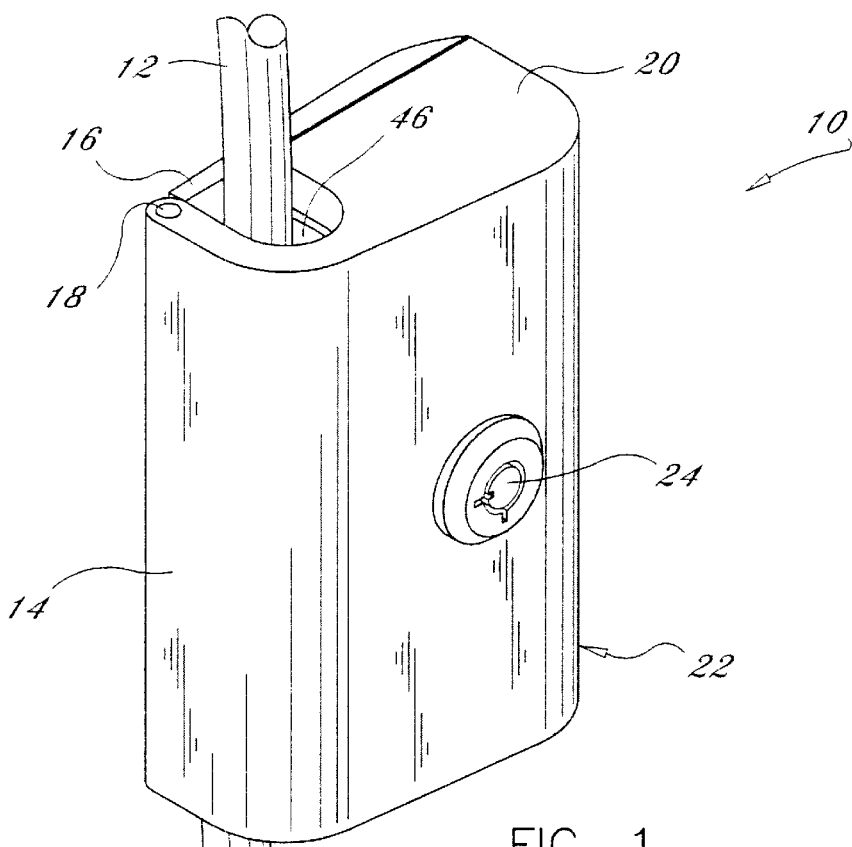
FIG. 1 illustrates a perspective view of the preferred embodiment in use.

These figures are illustrative only and are not intended to be limiting in any way.

DETAILED DESCRIPTION OF THE INVENTION

An anti-theft device for a device having a tube, cannula or hose member, which is preferably flexible, such as an endoscope, boroscope or other device is provided. The anti-theft device is generally designated as reference numeral 10. Device 10 is secured to tube portion 12 of an endoscope, boroscope, or other device, to prevent theft of such device. Device 10 preferably includes a top portion 14 which can be hingeably attached to a bottom portion 16 by a hinging mechanism 18. Other pivotable and non-pivotable attachment mechanisms can be used and are considered within the scope of the invention. As illustrated in FIGS. 1–3 and 5–9, hinging mechanism 18 may be a pin situated within holes through interlocking pieces of the top portion 14 and the bottom portion 16. Other hinging mechanisms known in the art can also be used and are also considered within the scope of the invention. Tube 12 extends from a first end 20 to a second end 22 of device 10. Top portion 14 is preferably provided with a locking mechanism 24.

Figure 2:
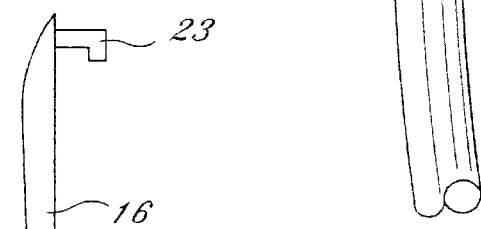
FIG. 2 is a top view of the invention in an unlocked/open configuration.
Figure 2:
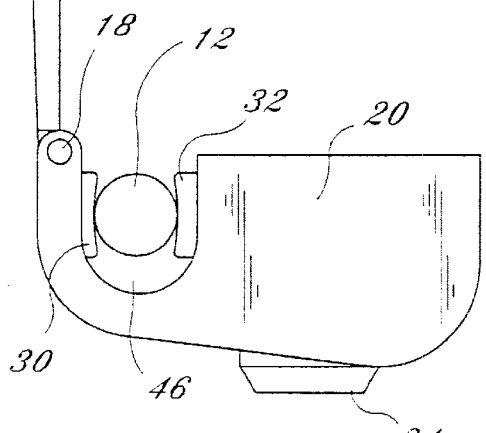
Figure 3:
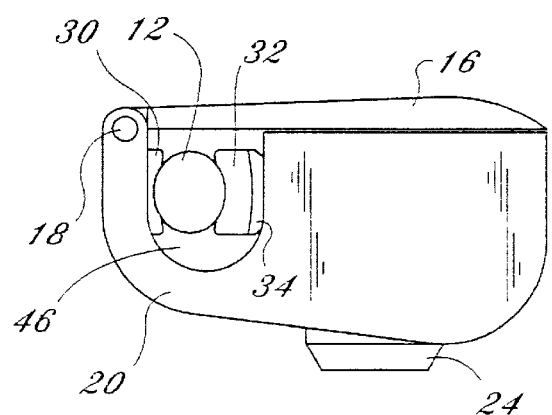
FIG. 3 is a top view of the invention in a locked/closed configuration.
Figure 9:
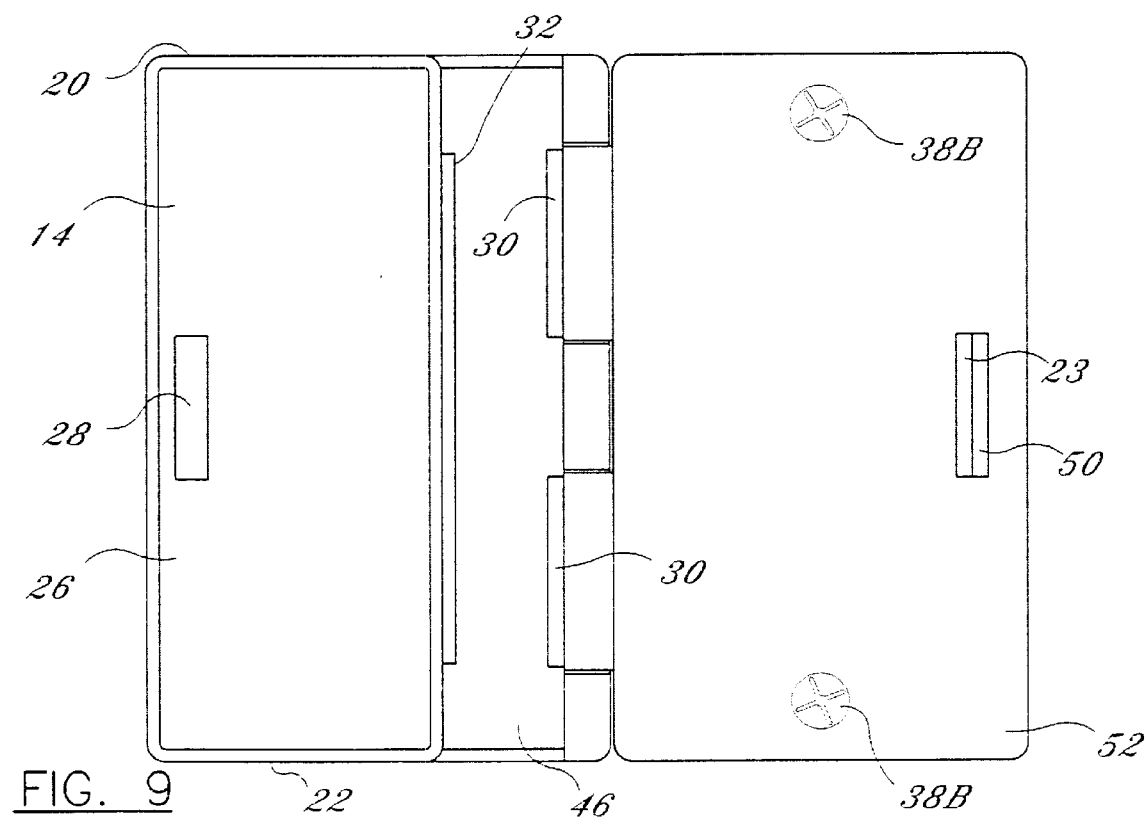
FIG. 9 is a top view of one embodiment of the invention in an open configuration.

As best seen in FIG. 2, bottom portion 16 includes a flange 23. Top portion 14 can include a cover plate 26 that fits over locking mechanism 24 to hide and protect locking mechanism 24. As best seen in FIG. 9, cover plate 26 includes a slit 28 that fits and mates with flange 23 when device 10 is in a closed position. An additional slit 50 may be provided next to flange 23 and is provided for easier manufacture of device 10.

As shown in FIGS. 2, 3, 6 and 8, tube 12 lies between a fixed resting surface 30 and a movable pressing surface 32. Resting surface 30 and pressing surface 32 are located in a channel 46 defined by top portion 14. Channel 46 extends from first end 20 to second end 22. Pressing surface 32 can include one or more contact areas pressing against the tube 12. Likewise, resting surface 30 may also include one or more contact areas. Resting surface 30 may be integral with a portion of the surface of channel 46 or may be attached to channel 46.

In the locked configuration, pressing surface 32 engages against the tube 12. Locking mechanism 24 upon activation rotates a cam 42. Activation is preferably accomplished through an appropriate key. Cam 42 engages a bolt 34 that forces pressing surface 32 against the tube 12. Pressing surface 32 may be an intrinsic part of bolt 34 or attached to bolt 34. The activation of locking mechanism 24 also rotates a locking lip 44 (See FIGS. 7 and 8). As shown in these figures, in the preferred embodiment, cam 42 and locking lip 44 are attached to locking mechanism 24 by a conventional attached mechanism 46, such as, but not limited to, a pin or nut/bolt combination.

Figure 8:
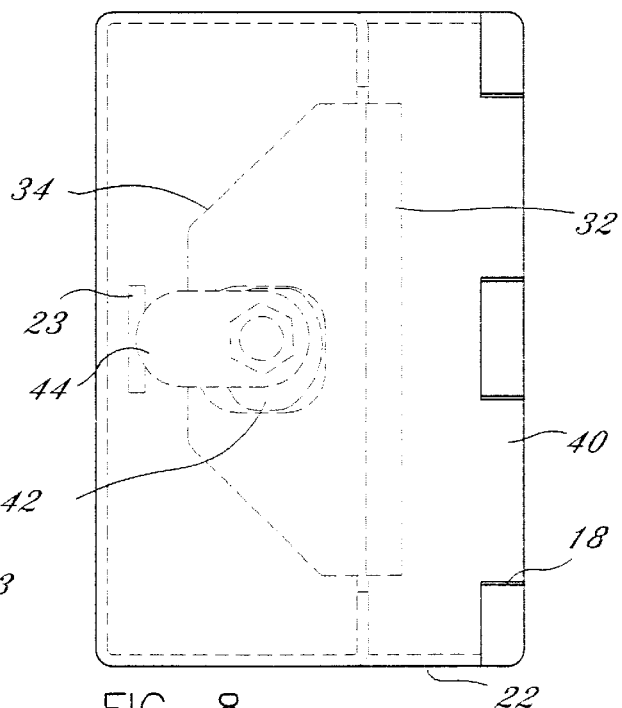
FIG. 8 is a top view of the invention in a closed and locked configuration.

Locking lip 44 located of top portion 14 overlaps flange 23 on bottom portion 16 when device 10 is closed and locked (See FIG. 8). Where cover plate 26 with slit 28 is provided, when device 10 is closed, flange 23 fits through slit 28 and sits below locking lip 44. Thus, when locking mechanism 24 is activated, cam 42 rotates, thereby pressing the bolt 34 toward tube 12 and rotating locking lip 44 so that locking lip 44 overlaps the flange 23.

As mentioned above, attachment mechanism 48 for attaching 48 cam 42 and locking lip 44 to locking mechanism 24 may be a nut around a bolt. The bolt can fit inside a hole through cam 42 and a hole through locking lip 44. Cam 42 may include a notched portion to fit locking lip 44 to help ensure that locking lip 44 rotates with the rotation of cam 42. As also mentioned above, other attachment mechanisms for attaching locking mechanism 24 to cam 42 and the locking lip 44 can also be provided. These alternative embodiments include combining locking mechanism 24, cam 42 and locking lip 44 elements combined into a single element, or a subcombination of these components into one element.

Figure 4:
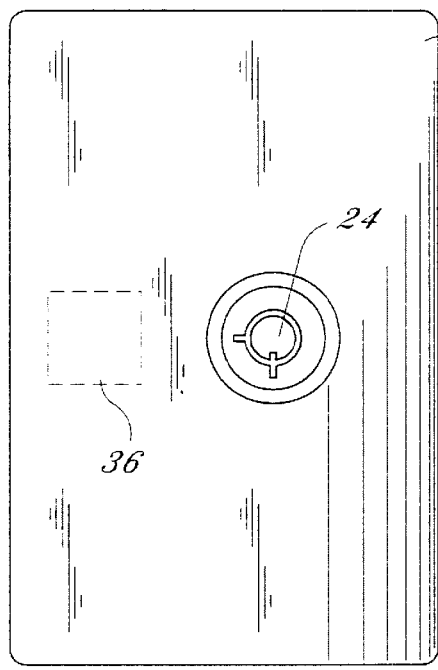
FIG. 4 is an overhead view of the invention in a closed and locked configuration.

One or more security sensors 36 (FIG. 4) as are generally known in the art may be attached to the device 10. Sensor(s) 36 activate a conventional alarm system. (not shown) when the anti-theft device is removed from its designated area without authorization. Sensor 36 can be placed on the outer surface of top portion 14, as shown in FIG. 4. However, other locations for sensor 36, either on the surface or elsewhere on device 10, can be used and are considered within the scope of the invention.

Figure 5:
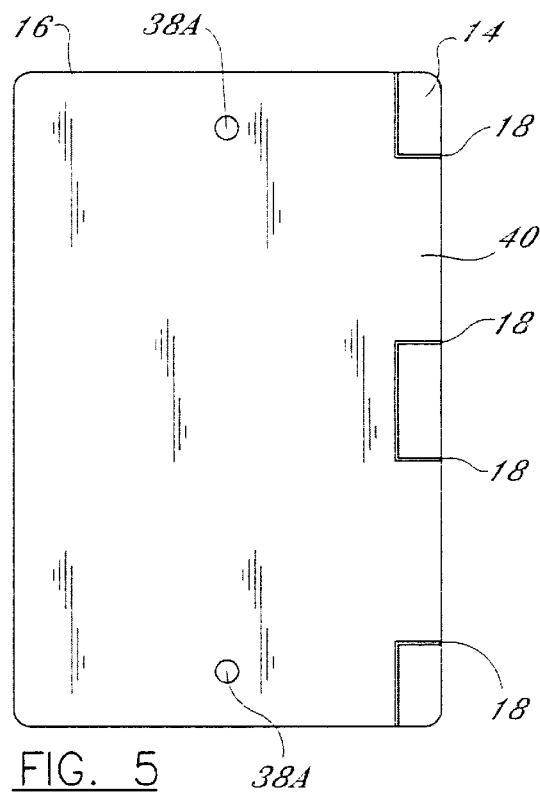
FIG. 5 is a bottom view of the invention in a closed configuration.
Figure 6:
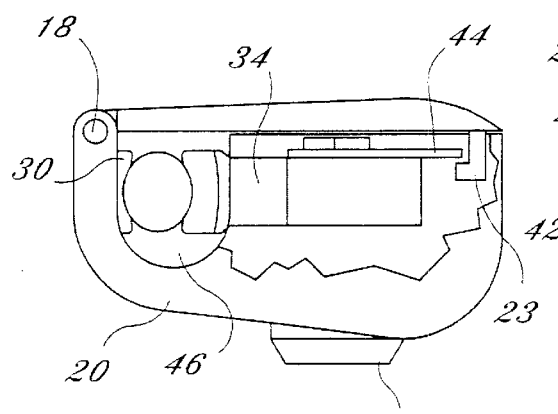
FIG. 6 is a top cut-out view of the invention in a closed configuration.
Figure 7:
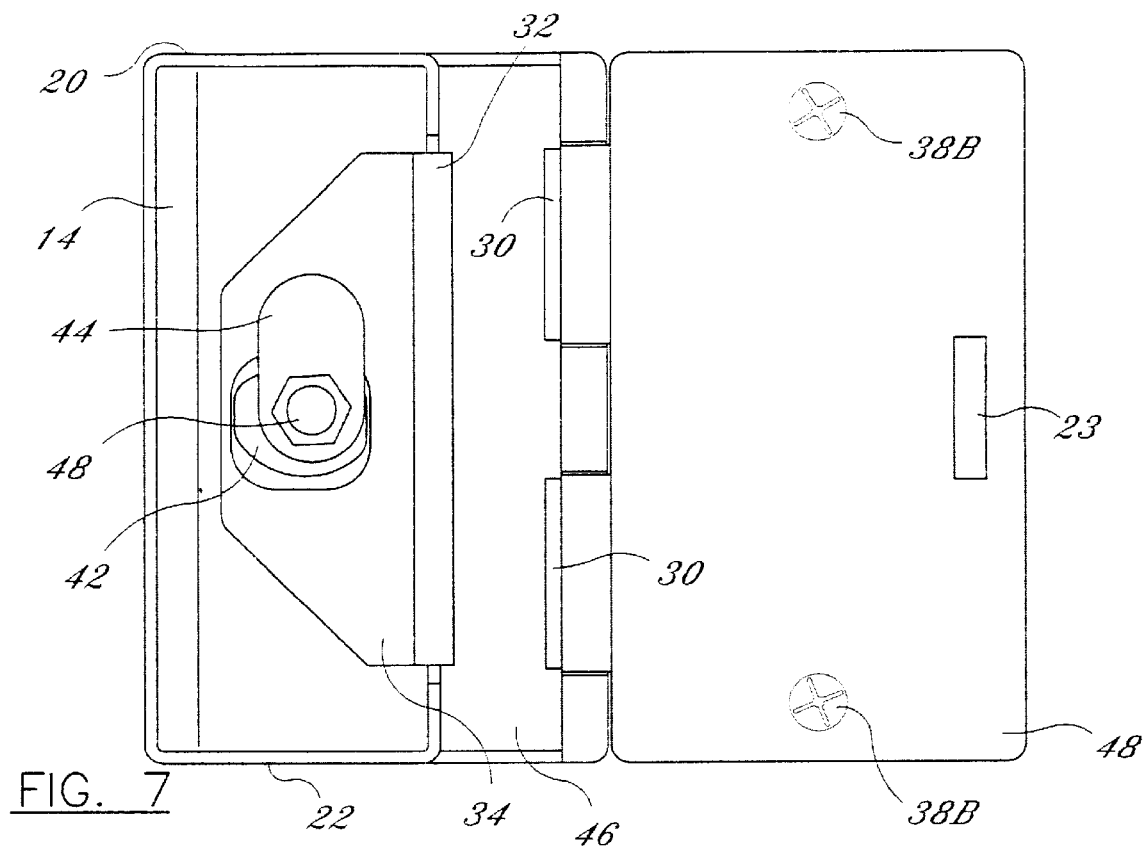
FIG. 7 is an overhead view of the invention in an open configuration.

Additionally, a means for securing 38 device 10 to a wall other point or structure can be provided. As shown in FIGS. 5, 7 & 9, means for securing 38 may be one or more holes 38A extending through an inner surface 52 and an outer surface 40 of bottom portion 16 and a similar number of screws 38B, with each screw 38B associated with a hole 38A. As shown, the heads of the screws. 38B are larger in diameter than the diameter of holes 38A and are placed at and abut with inner surface 52 of the bottom portion 16, so that the screw tip goes through outer surface 40 of bottom portion 16 for insertion into the designated wall or other structure. Other means for securing 38 the device 10, both removable and permanent, can also be used and are considered within the scope of the invention.

Device 10 can be attached to a wall adjacent to where endoscopes or other devices are normally hung when not in use, such that it is relatively easy to attach anti-theft device 10 to a portion of tube 12 of the device to be locked as described above, while permitting the remaining portion of the endoscope or other device to maintain its hanging or resting position.

If anti-theft device 10 is removed without permission without the use of locking mechanism 24, such as by cutting device 10, in all likelihood the endoscope or locked device will be damaged and thus reduce the value of the endoscope, which obviously deters this type of removal and increases the effectiveness of device 10.

Top portion 14 and bottom portion 16 of device 10 are preferably constructed from a rigid material such as plastic, metal, fiberglass, etc.

It is also within the scope of the invention to construct the bottom portion such that it defines the channel and receives the locking components described above, while also still being able to be secured to the wall or other surface.

The term "tube" in the disclosure and claims is intended to cover tubes, hoses, flexible cannulas and similar devices.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An anti-theft device for a device having a flexible tube, said anti-theft device comprising:

a bottom portion;

a top portion, said top portion defining a channel extending from a first end of said top portion to a second end of said top portion, said channel adapted for receipt of a portion of a flexible tube;

a locking assembly for locking said top portion to said bottom portion, said locking assembly including a locking mechanism disposed within said top portion;

a movable pressing surface and a fixed resting surface both disposed within said top portion;

wherein said pressing surface is controlled by said locking mechanism;

wherein upon turning of the locking mechanism to lock said top portion to said bottom portion, said pressing surface is moved inward into said channel and forces at least a portion of the flexible tube disposed within said channel against the resting surface;

wherein when said top portion is locked to said bottom portion said pressing surface and said resting surface securely retain said at least a portion of the flexible tube within said channel and from any substantial movement.

2. The anti-theft device of claim 1, wherein said locking assembly includes a flange attached to said bottom portion that extends into said top portion when in the closed position.

3. The anti-theft device of claim 2, further including a locking lip disposed within said top portion; wherein upon turning of said locking mechanism to its locked position said locking lip turns and extends above said flange to prevent said top portion from being removed from said top portion's locked relationship with said bottom portion.

4. The anti-theft device of claim 1, further including a cam and a bolt disposed within said top portion, said pressing surface attached to said bolt; wherein upon turning of said locking mechanism said cam pushes said bolt causing said pressing surface to force at least a portion of the flexible tube securely against the resting surface.

5. The anti-theft device of claim 1 wherein said top portion is pivotally connected at a first side to a first side of said bottom portion such that said top portion remains attached to said bottom portion in an open position and in a closed position.

6. The anti-theft device of claim 1, further including a sensor attached to said top portion.

7. The anti-theft device of claim 1, wherein further including a means for securing said bottom portion to a surface.

8. The anti-theft device of claim 7, wherein the surface is a wall.

9. The anti-theft device of claim 1, wherein said locking mechanism comprises:
    a locking lip;
    a cam; and
    means for attaching the locking lip and the cam to the locking mechanism.

10. The anti-theft device of claim 2, wherein said top portion further includes a plate that fits over said locking mechanism; wherein said plate includes a slit that receives the flange of said bottom portion in the closed position.

11. The anti-theft device of claim 1, wherein the locking mechanism is activated by a key.

12. The device of claim 2, wherein said bottom portion including a slit adjacent to the flange.

13. An anti-theft device for a device having a flexible tube, said anti-theft device comprising:
    a top portion, said top portion defining a channel extending from a first end of said top portion to a second end of said top portion, said channel adapted for receipt of a portion of a flexible tube, said top portion constructed from a substantially rigid material;
    a bottom portion pivotally attached at a first side to a first side of said top portion such that said top portion remains at all times attached to said bottom portion in an open position and in a closed position, said bottom portion constructed from a substantially rigid material; and
    a locking assembly for locking said top portion to said bottom portion, said locking assembly including a locking mechanism disposed within said top portion;
    a movable pressing surface and a fixed resting surface both disposed within said top portion;
    wherein said pressing surface is controlled by said locking mechanism;
    wherein upon turning of the locking mechanism to lock said top portion to said bottom portion, said pressing surface is moved inward into said channel and forces at least a portion of the flexible tube disposed within said channel against the resting surface;
    wherein when said top portion is locked to said bottom portion said pressing surface and said resting surface securely retain said at least a portion of the flexible tube within said channel and from any substantial movement.

14. The anti-theft device of claim 13, wherein said locking assembly includes a flange attached to said bottom portion that extends into said top portion when in the closed position.

15. The anti-theft device of claim 14, further including a locking lip, a cam and a bolt all disposed within said top portion, said pressing surface attached to said bolt; wherein upon activation of said locking mechanism said locking lip turns and extends above said flange in the closed position to prevent said top portion from being removed from said top portion's attachment to said bottom portion and said cam pushes said bolt causing said pressing surface to force at least a portion of the flexible tube securely against the resting surface.

16. The anti-theft device of claim 14, wherein said top portion further includes a plate that fits over said locking mechanism; wherein said plate includes a slit that receives the flange of said bottom portion in the closed position.

17. An anti-theft device for a device having a flexible tube such as an endoscope or boroscope, said anti-theft device comprising:
    a top portion, said top portion defining a channel extending from a first end of said top portion to a second end of said top portion, said channel adapted for receipt of a portion of a flexible tube, said top portion constructed from a substantially rigid material;
    a bottom portion pivotally attached at a first side to a first side of said top portion such that said top portion remains at all times attached to said bottom portion in an open position and in a closed position, said bottom portion constructed from a substantially rigid material, said bottom portion including a flange extending into said top portion when in the closed position, said top portion having a plate that fits over said locking mechanism, said plate including a slit that receives the flange of said bottom portion in the closed position;
    a locking mechanism disposed within said top portion for locking said top portion to said bottom portion;
    a movable pressing surface and a fixed resting surface disposed within said top portion;
    a locking lip disposed within said top portion,
    a cam disposed within said top portion; and
    a bolt disposed within said top portion, said pressing surface attached to said bolt;
    wherein upon turning of said locking mechanism to lock said top portion to said bottom portion said locking lip turns and extends above said flange to prevent said top portion from being unlocked from its attachment to said bottom portion and said cam pushes said bolt causing said pressing surface to force at least a portion of the flexible tube securely against the resting surface;
    wherein when said top portion is locked to said bottom portion said pressing surface and said resting surface securely retain said at least a portion of the flexible tube within said channel and from any substantial movement.

* * * * *